United States Patent [19]

Popovic et al.

[11] Patent Number: 5,115,808
[45] Date of Patent: May 26, 1992

[54] METHOD AND DEVICE FOR NONINVASIVE ACOUSTIC TESTING OF ELASTICITY OF SOFT BIOLOGICAL TISSUES

[75] Inventors: Goran Popovic, Belgrade, Yugoslavia; Armen Sarvazyan; Viktor Ponomarjev, both of Pushchino, U.S.S.R.; Dusan Vucelic, Belgrade, Yugoslavia

[73] Assignees: Institute of General and Physical Chemistry, Belgrade, Yugoslavia; Institute for Biological Physics of the USSR Academy of Science, Pushchino, U.S.S.R.

[21] Appl. No.: 526,818

[22] Filed: May 22, 1990

Related U.S. Application Data

[63] Continuation-in-part of Ser. No. 234,330, Aug. 18, 1988, Pat. No. 4,947,841.

[51] Int. Cl.⁵ .............................................. A61B 8/00
[52] U.S. Cl. .................................. 128/660.02; 128/774
[58] Field of Search ....................... 128/660.02, 774; 73/597

[56] References Cited

U.S. PATENT DOCUMENTS

| | | | |
|---|---|---|---|
| 4,217,912 | 9/1980 | Hubmann et al. | 73/574 X |
| 4,250,894 | 2/1981 | Frei et al. | 128/774 |
| 4,777,599 | 10/1988 | Durogi et al. | 128/774 X |
| 4,790,188 | 12/1988 | Bussiere et al. | 73/597 |
| 4,799,498 | 1/1989 | Collier | 128/774 |
| 4,947,851 | 8/1990 | Sarvazyan et al. | 128/660.02 |

Primary Examiner—Francis Jaworski
Attorney, Agent, or Firm—Helfgott & Karas

[57] ABSTRACT

A method and device for non-invasive acoustic testing of elasticity of soft biological tissues, wherein a tangential oscillatory deformation is induced on the surface of a tissue being tested and only those oscillations, out of all resulting oscillations are measured, which occur in the direction of the induced deformation, and wherein a Young's modulus for the direction and anisotropic characteristics of the elasticity of tissue being tested are determined from a characteristic of those oscillations.

11 Claims, 9 Drawing Sheets

METHOD AND DEVICE FOR NONINVASIVE ACOUSTIC TESTING OF ELASTICITY OF SOFT BIOLOGICAL TISSUES

CROSS-REFERENCE TO RELATED APPLICATION

This application is a continuation-in-part of application Ser. No. 234,330 filed Aug. 18, 1988 and now U.S. Pat. No. 4,947,851.

BACKGROUND OF THE INVENTION

The present invention relates to a method and device for testing elastic properties of soft biological tissues. More particularly, the present invention relates to an acoustic device and method for noninvasive measurement of the velocity of surface acoustic waves in tissues thus providing estimating of the shear elastic properties of tissues for the purposes of medical diagnosis.

The viscoelastic properties of biological tissues are directly related to their structural organization. It was found that bulk elastic properties of tissues are mainly determined by their molecular composition, while shear elasticity is characteristic of higher levels of structure. Physiological processes in an organism may result in structural changes in tissues that can be detected by measuring their shear elastic properties.

The methods of testing viscoelastic properties of tissues are essentially based on invasive measurements on isolated samples. Maxwell, for example, employed torsional vibrations of a sample cut in the form of cylindrical rod fixed at one of the ends (Maxwell B. ASTM Bull #215 76, 1956). Shear modulus was determined by measuring the magnitude of force necessary to provide a given deformation at the other end of the rod. The range of working frequencies was 0.002 to 200 kHz.

For measuring the bulk elastic properties, i.e. the ultrasonic velocity and bulk compressibility of media, a great variety of methods using bulk acoustic waves in a high-frequency range were developed. For example, according to one of those methods (Nole A. W. Mowry S. C. J. Acoust. Soc. Amer., 20, 432, 1948) the speed of sound was evaluated from the measurement of time-of-flight of an acoustic pulse in the sample being tested which is immersed in a liquid between the ultrasonic transducer and reflector.

Among the known methods of noninvasive testing of bulk elastic properties of tissues in the method and device for noninvasive monitoring the instantaneous fluctuations in viscoelasticity-related properties of a living tissue (Benjamin Gavish, European Patent EP 0,135,325 A2, U.S. Pat. No. 4,580,574, T. 1065). The device comprises a pair of substantially parallel spaced-apart piezotransducers, one of them being adjustable with respect to the other to enable insertion and clamping of a segment of a living tissue therebetween. One transducer is connected to a high frequency generator and the other is attached through an amplifier and demodulator to a signal analyzer. The frequency of the ultrasonic resonant oscillations induced in a tissue and their magnitude are characteristic of the viscoelastic properties of the tissue.

The aforementioned method of testing the tissues makes it possible to detect certain physiological processes and particularly the changes in the microcirculation of blood. But since the subject of testing are the bulk elastic properties which may vary in tissues by no more than several per cent the accuracy of such a method would not be very high, as compared to the accuracy of the methods using the shear elasticity which may change in some cases by hundreds per cent, depending on the physiological state of a tissue. The method does not imply any means to control the force by which the transducers are pressed to a tissue sample placed in the gap therebetween. But such a pressure affects the properties of the samples and still increases the error of measurement. Besides, because it is often difficult to provide access to the tested tissue from the opposite sides, this technique is not applicable to most of the body.

It is impossible to evaluate by means of this method one of the important characteristics related to the structural organization of living tissues—their anisotropy, i.e. the difference in mechanical properties in various directions.

The possibilities of testing the shear elastic properties of biological tissues were investigated in the paper of V. A. Passechnik, A. P. Sarvazyan, "On the possibility of examination of the muscle contraction models by measuring the viscoelastic properties of the contracting muscle" Studia Biophysica, Berlin, Band 13, 1969, Heft 2, s 143–150. In this publication the changes in elastic properties of an isolated muscle during contraction were studied. The low frequency acoustic oscillations (450 to 1200 Hz) were excited in a sample by means of a flexural piezotransducer and received at a distance by the like piezotransducer. The tension of a muscle was measured in various phases of contraction. The modulus of shear elasticity was evaluated by measuring the amplitude and the phase of received signal.

According to the other method of testing the shear elasticity of tissues (R. O. Rotts, D. A. Christman, E. M. Buras: The dynamic mechanical properties of human skin in vivo, J. Biomechanics, Vol. 16, #6, pp. 365–372, 1983) the shear oscillations in tissue were produced by a "recorder" (a phonograph recording cutterhead) touching the tissue surface with its contact tip (stylus). A phonograph cartridge with a stylus was used as a receiver. Measurements were conducted in the frequency range of 200–1000 Hz. The recorder was excited by the white noise sound generator; the characteristic frequencies were estimated by means of a spectrum analyzer. The measured parameters were the velocity of propagation of shear waves and their attenuation. The authors of the cited research came to the conclusion that of the low frequency range investigated by said method, the mechanical waves excited in tissues are of shear character and are localized only in the superficial layer of the tissue, i.e. in the skin, and because of that only in this range it is possible to provide the selective measurement of skin elasticity, while at higher frequencies the measurement is more difficult to make because of the small depth of penetration of surface waves. This conclusion is disputable. Since the velocity of shear waves in soft tissues may be 5 to 50 m/s, the wavelength in the frequency range of about 1 kHz should be about 5 to 50 mm.

Since the penetration depth of surface waves cannot be much less than a wavelength, the subcutaneous structure elements and in some cases the bone tissue may affect the propagation of the waves of that range, therefore the selectivity of the method as related to measurement in skin seems rather doubtful.

The authors of said method (R. O. Rotts et al.) do not take into account a peculiarity of surface waves such as the dependence of the velocity and attenuation of a surface wave on the direction of propagation relative to the displacement vector of a tangential oscillation excited by the transmitter on the surface of tissue. Neither was mentioned the anisotropy which is the important feature of shear elasticity in biological tissues (in particular in skin).

The structure of tissues is subject to certain changes in a wide range of clinical situations. The structural changes are closely related to the change in viscoelastic properties of tissues. The bulk elastic properties are not particularly sensitive to the structure and its anisotropy as compared to the shear properties, so the testing of shear properties will prove to be of greater value for clinical medicine and diagnosis. What is therefore needed is a method for noninvasive and highly sensitive testing of shear properties of a tissue along the chosen direction.

SUMMARY OF THE INVENTION

It is an object of the present invention to provide a method of determination of a modulus of elasticity of anisotropic structures by defining maximum and minimum values of a modulus of elasticity determined in all directions of excitation of D-waves (as explained hereinafter), in accordance with a suggested mechanical model of anisotropy of the elastic tissue.

It is a further object of the present invention to provide a method of non-invasive determination of Young's modulus for a surface, the testing of which is not possible with known methods.

The present invention is directed to the determination of the modulus of elasticity by the characteristics of so-called D-waves (directed waves) as opposed to pure shear waves used in conventional acoustical methods of testing tissues of human skin.

Figure 15:
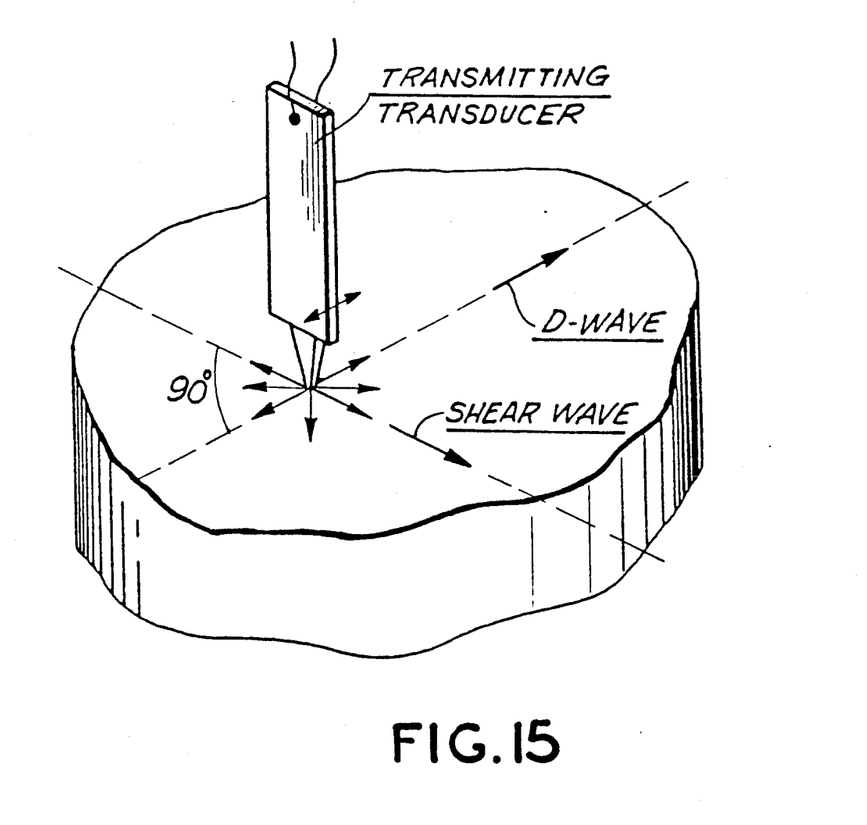
FIG. 15 shows two types of waves propagated across the surface of an elastic media.

FIG. 15 shows the directions of propagation of shear waves and D-waves (directed waves) on the surface of an elastic media.

D-waves can propagate only along the surface of an elastic media, when a tangential deformation is induced as shown in FIG. 15. These waves propagate across the surface of the media in a direction X of an induced tangential deformation. The wave, propagating on the surface in other directions, has properties of D-waves only partially.

One of the specific properties of D-waves is that the speed of propagation in isotropic media is two times greater than the speed of a pure shear wave (traveling in direction X). Another specific property of D-waves is that the speed of propagation of D-waves is sensitive to anisotropic property of media in the form of fibrous structures, positioned on the surface level, e.g. fibers of colagen in skin. If the direction of the propagation of D-waves coincides with the direction of elongation of the fibrous structures, the speed of propagation can be greater, depending on the elasticity of the fibers and their quantity. The pure shear waves do not have such specific properties of the D-waves.

The differences in specific properties of D-waves and pure shear waves reside in that D-waves excite in thin fiber structures symmetric Lamb-waves, the speed of which depends only on the elastic properties of the fibers and does not depend on the cross section area of the fibers. Waves with a perpendicular deformation, pure shear waves, excite in the thin fibers asymmetric Lamb-waves, the speed of which depends on the fiber cross section area and reduces to zero with the reduction of the cross section area.

The aforementioned objects of the present invention are attained by a method of noninvasive testing of anisotropic elasticity of a tissue comprising the steps of: inducing on the surface of a tissue being tested a tangential oscillatory deformation; measuring, out of all resulting oscillations of particles of the surface of the tissue being tested, only the oscillations which occur in the direction of the induced deformation, and determining from a characteristic of the measured oscillations a Young's modulus for the direction and anisotropic characteristics of the elasticity of a tissue being tested.

The aforementioned objects, features and advantages of the invention will, in part, be pointed out with particularity, and will, in part, become obvious from the following more detailed description of the invention, taken in conjunction with the accompanying drawing, which form an integral part thereof.

DETAILED DESCRIPTION OF THE PREFERRED EMBODIMENTS

Figure 1:
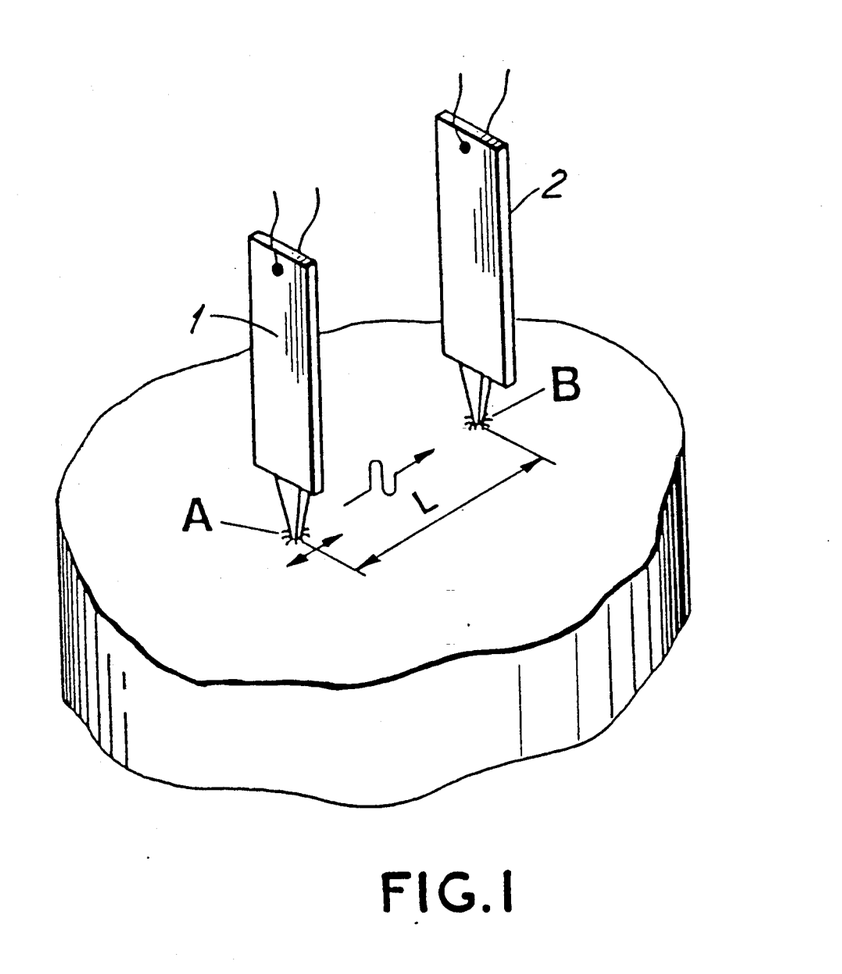
FIG. 1 is an illustration of the principle of the method according to the invention.

In the method of the present invention, the transmitting and receiving flexural bimorphous piezotransducers having the contact tips on their ends are brought into mechanical contact with a tissue being investigated. Providing an electrical pulse to the transmitter excites a damped tangential oscillation in the matter close to the contact tip of the transmitter, with a frequency in the range of 0.5 to 30 kHz, depending on the construction of the transducer and the properties of the matter. The propagating mechanical oscillation excites an electric signal in the receiver. The velocity of propagation is determined by measuring the time required for a pulse of tangential deformation to travel the distance between the transmitter and the receiver. The velocity and attenuation of a shear wave depends on the angle between the direction of propagation and the vector of displacement of the tangential oscillations excited by the transmitter. The wave propagating along the vector of displacement has the maximum velocity and the minimum attenuation. This is the reason for placing the transmitter and receiver as shown in FIG. 1, where 1 and 2 are the transmitting and receiving flexural bimorphous piezotransducers; the vectors of displacement in both transducers coincides with the line connecting the contact tips A and B.

The use of bimorphous piezotransducers offers the optimal acoustic matching with the tested tissue and their vertical position with respect to the surface of the tissue tested provides for the possibility of measurement of tangential deformation of that surface and also the possibility of receiving only the oscillations of the particles of the surface which occur in a direction of induced initial deformation of the surface.

The measurement of the speed of sound, which travels only in the direction A-B (FIG. 1) enables the determination of surface modulus of Young of the tested tissue, which is sensitive to the thin fiber structures laying on the surface of the tissue.

Figure 2A:
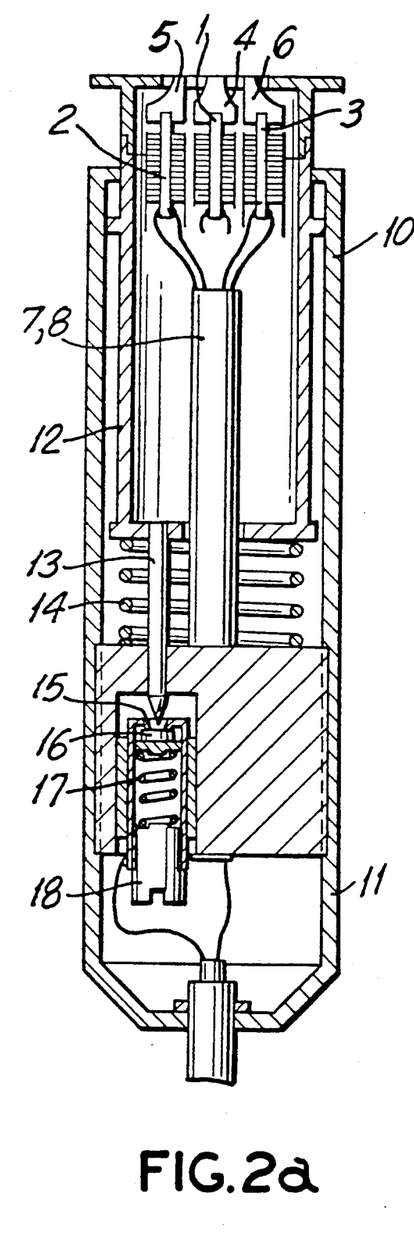
FIG. 2a is a cross-sectional view of the probe.
Figure 3:
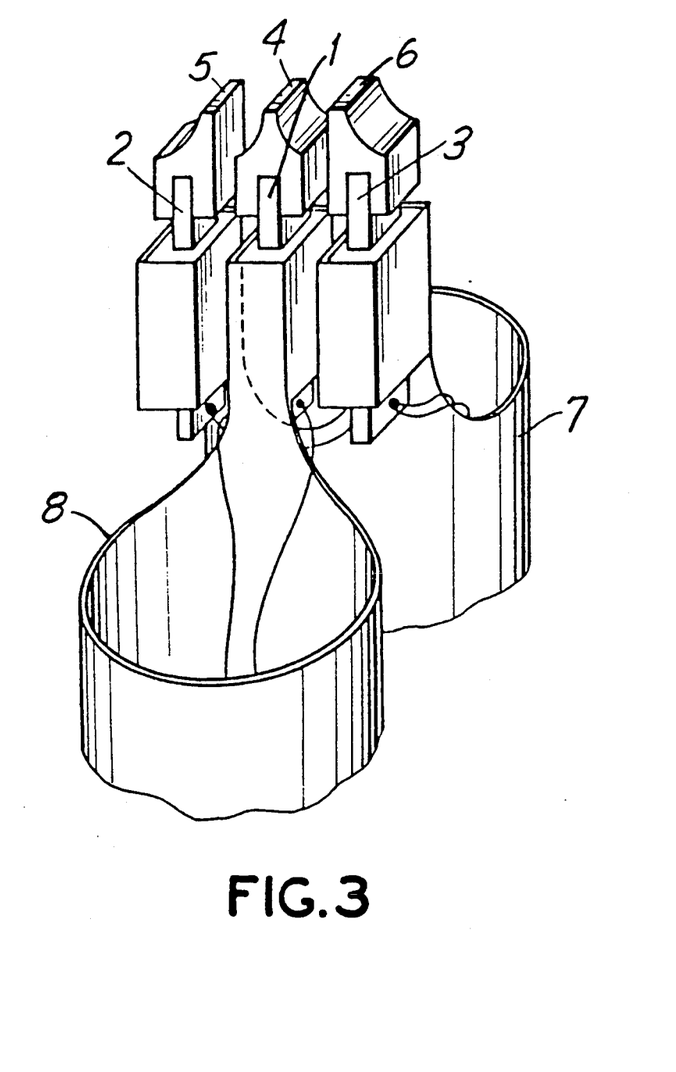
FIG. 3 shows the arrangement of the transducers with their contact tips.

In the preferred embodiment, the device for measuring the velocity comprises a probe with one transmitting and two receiving piezotransducers, the receiving transducers being placed symmetrically with respect to the transmitter as shown in FIGS. 2a and 3. Using two receivers instead of single one allows for the differential amplification of the received acoustic signals; this is important because the signal felt by the receiver is small.

The three piezotransducers 1, 2, 3 with contact tips 4, 5, 6 are mounted onto the probe as shown in FIGS. 3 and 2a by means of acoustic delay lines 7 and 8 in the form of hollow thin-wall metallic shafts. The length of the shafts is great enough to delay the acoustic signal passing from the transmitter to the receiver through the body of the probe for a time several times greater than the propagation time in the intended media. The transducers 1, 2, 3 are fixed in the shafts 7 and 8 by means of damping elastic gaskets, all together being placed inside a protective case 12 which serves at the same time as a pressure sensor for standardizing the force by which the probe is pressed to the matter. The case 12 drives a three-state switch (FIG. 2b) comprising a needle contact 13, a spring 14, an immobile tubular contact 15 fixed through insulator plastic gasket in a base 9, and a mobile contact plate 16, normally pressed to the contact 15 by a spring 17 separated by an insulator plate.

Figure 2B:
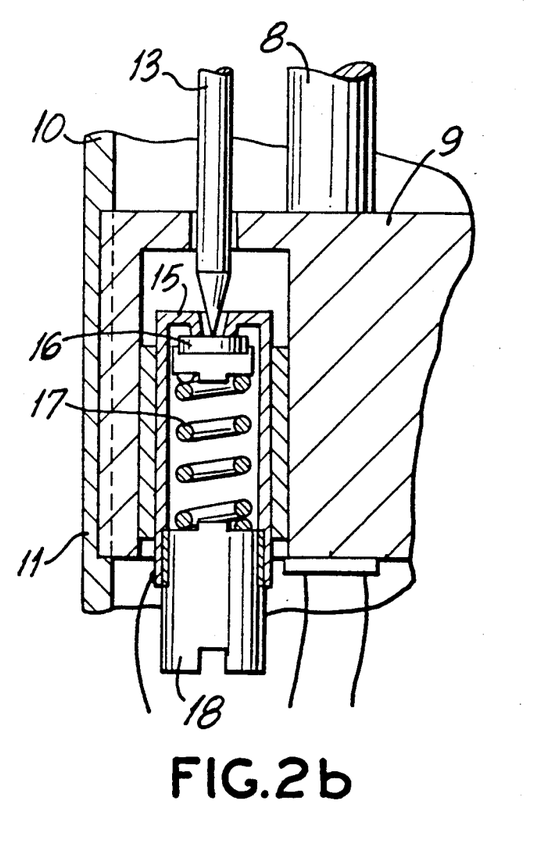
FIG. 2b shows a unit of FIG. 2a for standardizing a force by which the probe is pressed to a tissue.

The switch is normally open. During the operation, it may be switched on only in the case where the force compressing the spring 17, i.e. the force by which the probe is pressed against the matter, is great enough to make the needle 13 touch the plate 16 but still is not so great as to break the contact between the plate 16 and the tubular contact 15. According to said hereabove, the lower limit of force is determined by the spring 14 which is adjusted by displacing the threaded base 9 inside the exterior case 10, while the upper limit of the force is adjusted by the spring 17 which is compressed by a screw 18. The admitted range of the force may be made almost as small as the hysteresisis of friction inside the contact unit. It must be large enough though, so as to be easily controlled by hand.

The case 12 and the transducers are arranged so that in the admitted range of force, the contact tips 4, 5 and 6 occupy a fixed position close to the plane of the working edge of the probe.

Figure 4A:
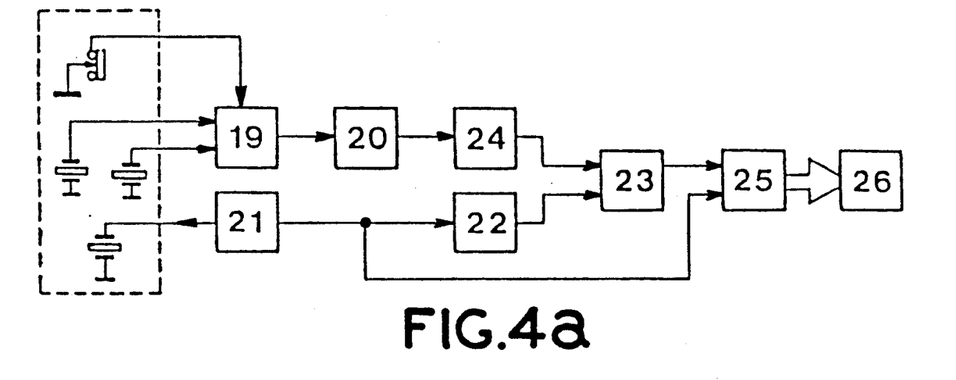
FIGS. 4a, 4b and 4c show circuit block diagrams.
Figure 5:
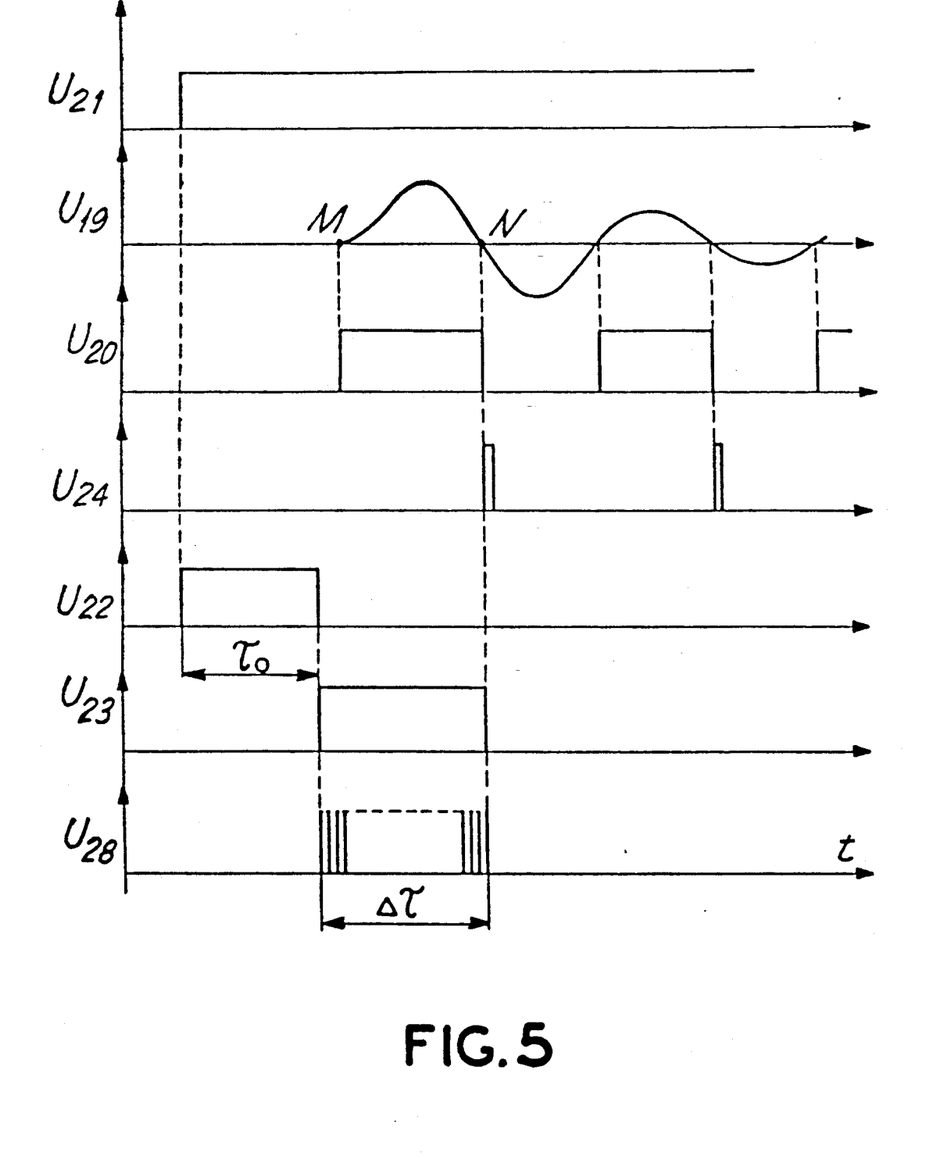
FIG. 5 is the clock diagram of the basic measurement cycle.

The switch enables the operation of the electronic block (see FIG. 4a) comprising a differential input amplifier 19, a chip 20, a bistable (type 74121) circuit 24, a flip-flop circuit 23, a pulse generator 21, a delay unit 22, a processing unit 25 and a display unit 26. The pulse generator 21 provides the pulses exciting a flexural deformation in the transmitting piezotransducer; a 30 ms pause between the pulses comprises the elementary measurement cycle (see FIG. 5). When all the tips of the probe are brought into a contact with the matter being tested, the two counterphase electric signals induced in the receivers are sensed at the inputs of the differential amplifier 19. At the same time, the pulse from the generator 21 via the calibrating delay unit 22 sets the flip-flop circuit 23 which gates the count in the processing unit 25. The output of the amplifier 19 is limited by the chip 20 so as to form the pulses with abrupt edges as shown in FIG. 5. The leading edge of the first pulse corresponds to the front of the acoustic wave being first detected by the receiver (event M in FIG. 5), and the trailing edge corresponds to the wave's first passing the zero (unexcited) level (event N). Since the front of an acoustic wave is very smooth and difficult to be detected with enough confidence, the event N is used instead to measure the time-of-flight of the acoustic pulse between the transmitter and the receiver. The trailing edge of the pulse U20 associated with that event resets the flip-flop circuit 23 via the bistable circuit 24 thus disabling the count in the processing unit 25.

Figure 4B:
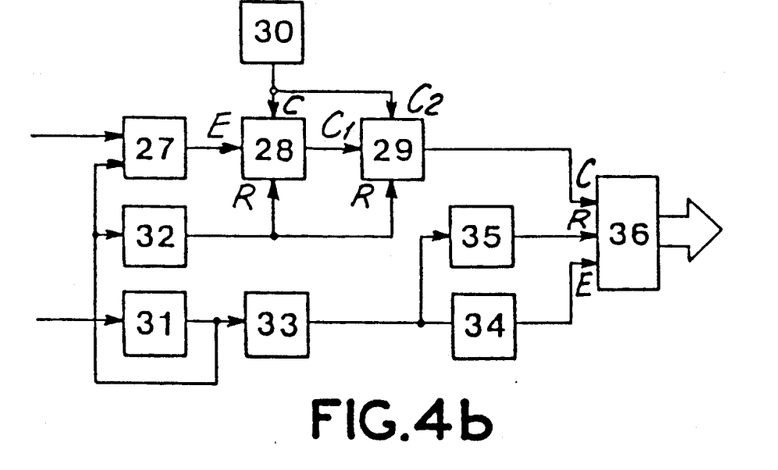

The processing unit 25 is shown in FIG. 4b. It performs the averaging of several measurements of time-of-flight of acoustic pulses and converting the average time into velocity of pulses. It consists of a frequency divider 28 gated through an AND latch 27 by a counter of samples 31, a time/velocity converter 29, a clock generator 30, a counter 36, bistables 32 and 35 and a NOT gate element 33.

Figure 4C:
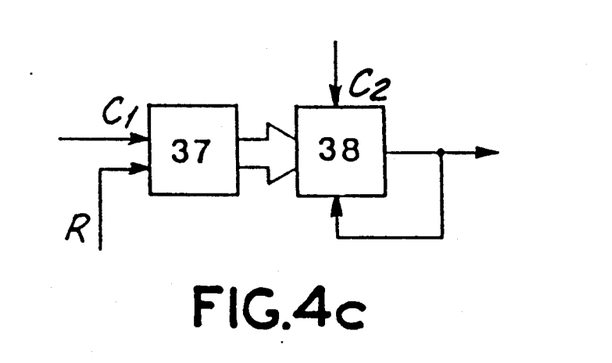

The possible implementation of the converter unit 29 is shown in FIG. 4c.

The frequency divider 28 together with a counter 37 accumulate the total number of clock pulses during several sampling periods; the divider 28 divides that number by the number of samples. The cycle of the counter 31 is twice the number of samples; during the first half of a cycle its output is HIGH, thus enabling (via latch 27) the sampling in counters 28 and 37. When the output of counter 31 goes LOW, the sampling stops with the average value of time being stored in counter 37. At the same time, the output of the invertor 33 goes HIGH thus enabling the count in the buffer counter 36 for a certain period measured by a timer 34. The 36 counts the output of the presettable subtracting counter 38 which runs permanently loading the value from counter 37 each time its count goes down to zero, thus providing the pulses with the frequency being the inverse value of the value of time stored in 37. The timer 34 gates those pulses to the counter 36; it is adjustable to provide the means, together with the adjustable delay unit 22, for calibrating the velocity of pulses. The value of velocity accumulated in counter 36 is displaced by the display unit 26. At the end of sampling/display cycle the output of 31 again goes HIGH thus resetting via bistables 32 and 35 the counters 28, 37, 36 and enabling the sampling via latch 27.

According to the present invention the prototype was made to demonstrate the possibilities of the proposed method in different experiments. In Table 1 one can see how the velocity of surface wave may vary over the skin of a human body.

TABLE 1

| | The velocity of shear wave, m/s | | | |
|---|---|---|---|---|
| Forehead | Cheek | Chest | Tip of finger | Skin |
| 28 ± 5 | 20 ± 3 | 21 ± 5 | 60 ± 10 | 35 ± 8 |

Another example is in the measurement of the elasticity of human skin before and after the cryomassage. In a group of women chosen by a cosmetologist as having specifically thin skin on their faces the velocity of surface wave measured before the cryomassage was in the range of 20.2 m/s. Immediately after the cryomassage the velocity was in the range of 60 m/s; it returned to the initial value in about 10 minutes. The rate of relaxation of the electricity of skin after the cryomassage was shown to be specific for the particular type of skin.

One more example is the study of shear elasticity of muscle during contraction. In the isolated resting frog muscle, the velocity of propagation of shear wave along the fibers was about 10 m/s. During contraction it reached 35 m/s. The range of variance of shear wave velocity in the same biological tissue often exceeds 100 per cent, while in the case of bulk elastic waves the change is measured by several per cent.

It can be seen that the present invention provides the means for testing the tissues, highly sensitive to both the type of tissue and its physiological state, which may be extremely valuable in medical diagnosis, e.g. in diagnosing the skin pathology or in differentiation of normal and pathological tissues during surgical operations.

The experiments also showed that some features of the preferred embodiment prove to be advantageous and even necessary. Particularly, it should be mentioned that because of variety of reasons the force by which the probe is pressed to a tissue impacts to the mechanical state of tissues and strongly affects the results of measurement. The proposed feature of limiting the force makes this error nearly constant and allows it to be taken into account while calibration.

The other important feature is the use of two receivers instead of a single one. Besides the fact that it increases the sensitivity it is used to reduce the error that may occur during the manual application of the probe due to occasional shifts in relative position of the transmitting and the two receiving transducers since, it should be considered, the shafts carrying the transducers serve at the same time as acoustic delay lines and thus they must be essentially flexible. The maximum error occurs when the transmitter shifts towards one of the receivers; in this case, the signal comes to that receiver a little earlier than is expected, and same signal comes to the other receiver as later. The receipt of the signals is detected by their first passing the zero; provided the shift is small, the zero of the sum of the delay signal and the signal that comes in advance only slightly shifts from expected. This shift can be roughly estimated in the following way:

$$A \sin(\omega t + \psi) = A_1 \sin(\omega t + \phi) + A \sin(\omega t - \phi) \quad (4)$$

where: A is the amplitude of the resulting signal; $A_1$ and $A_2$ are the amplitudes of the signals in the receivers; $\psi$ is the phase shift of the resulting signal, which occurs due to non-symmetrical position of receiving contact tips, ±φ are the phase shifts of summed signals.

We can rewrite equation (4) in the following way:

$$A \sin(\omega t + \psi) = A_1 \sin\left[\omega t + \arctg\left(\frac{A_1 A_2}{A_1 + A_2}\right) tg\phi\right] \quad (5)$$

In the small range of displacement of the transmitter with respect to the center position between the receivers, the amplitude of the received signal may be considered as a linear function of the distance and, therefore, we can rewrite equation (5) as:

$$\sin(\omega t + \psi) \approx \sin\left[\omega t + \arctg\left(\frac{\Delta R}{R_o} tg\phi\right)\right] \quad (6)$$

where: $R_o$ is half the distance between the contact tips of the receiving piezotransducers, $\Delta R = L - R_o$ is the displacement of the transmitter relative to the contact tips of the receivers of the transmitter relative to the contact tips of the receiver.

Assuming f = 5 kHz, $R_o$ = 3 mm,
c = 40 m sec$^{-1}$
$\Delta R$ = 0.3 mm, where f is the working frequency and c is an average value of the velocity of surface waves in the human skin, taking into consideration said parameters (6) one can rewrite equation (6) as follows;

$$\sin(\omega t + \psi) \approx \sin\left(\omega t + \frac{\Delta R}{R} \cdot \phi\right) \quad (7)$$

It can be seen that by using two receiving piezotransducers instead of one, the error which occurs due to changes of the distance between contact tips of the transmitting and the receiving piezotransducers, is decreased approximately (ΔR/R) times, i.e. for the parameters given above the error for double-receiver device is ten times smaller than for one-receiver version of the device.

The modulus of elasticity of a tissue is determined by the measurement of the speed of an acoustic wave:

$$\sigma = \rho \cdot c^2 \quad (8)$$

where:
ρ—density of the tissue
σ—modulus of elasticity

Figure 6:
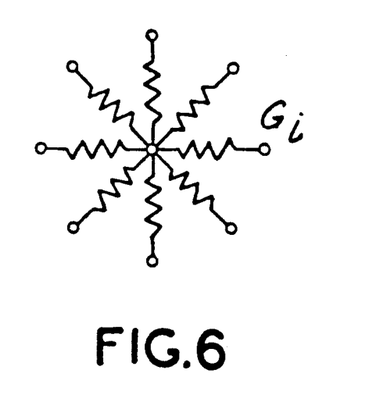
FIG. 6 schematically shows a mechanical model of biological tissues, which includes a combination of elastic elements.
Figure 7:
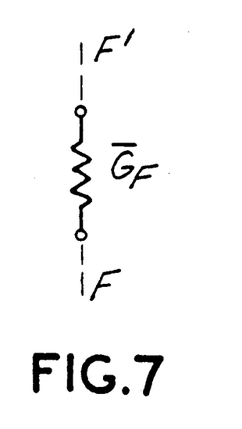
FIGS. 7 and 8 schematically show a model of a tissue with a unidirectional structure of fibers.
Figure 8:
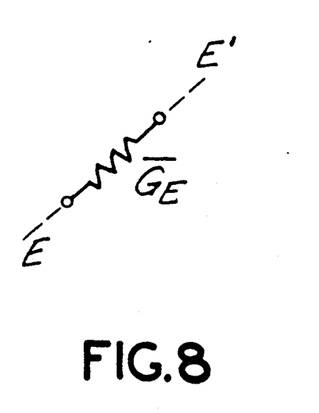

For the testing of anisotropic elasticity of biological tissues, a mechanical model of the tissues is herein suggested, which is comprised of a combination of discrete elastic elements G1 (springs) shown in FIG. 6. In this example, isotropic elasticity is a multidirectional combination of springs without a priority direction of skin elasticity. Every anisotropic structure made by a unidirectional structure of fibers is represented as an accordingly positioned spring, for example, as shown in FIGS. 7, 8.

The sum modulus of elasticity $\overline{\sigma}^*$ represents a geometric sum of different anisotropic modules of elasticity $\overline{\sigma}_j$ and isotropic modulus of elasticity $\sigma_i$ $$\overline{\sigma}^* = \Sigma \overline{\gamma}_j + \overline{\sigma}_i \quad (9)$$

Figure 9:
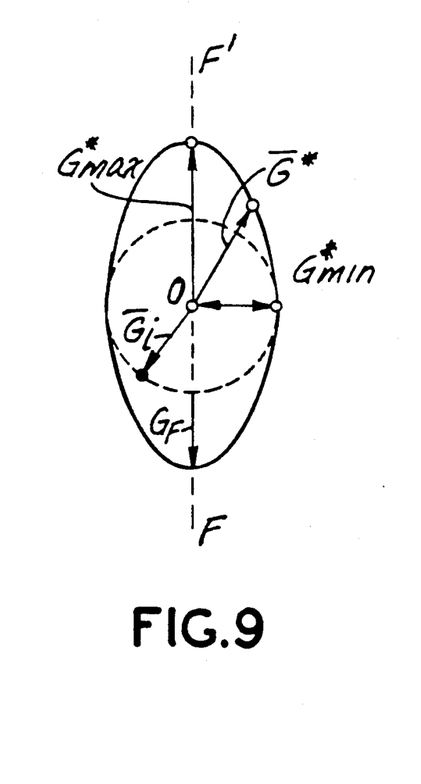
FIG. 9 illustrates a modulus of anisotropic elasticity for a unidirectional fiber structure.

In the case of unidirectional anisotropy the structure of which is determined in FIG. 9, the modulus of anisotropic elasticity is determined by the formula:

$$\sigma = \sigma^*_{max} - \sigma^*_{min} \qquad (10)$$

where
$\sigma^*_{max}$ is a maximum value of the sum modulus of elasticity, and
$\sigma^*_{min}$ is a minimum value of the sum modulus of elasticity.

The direction of anisotropy in that case coincides with the direction of a maximum of $\sigma^*$.

Figure 10:
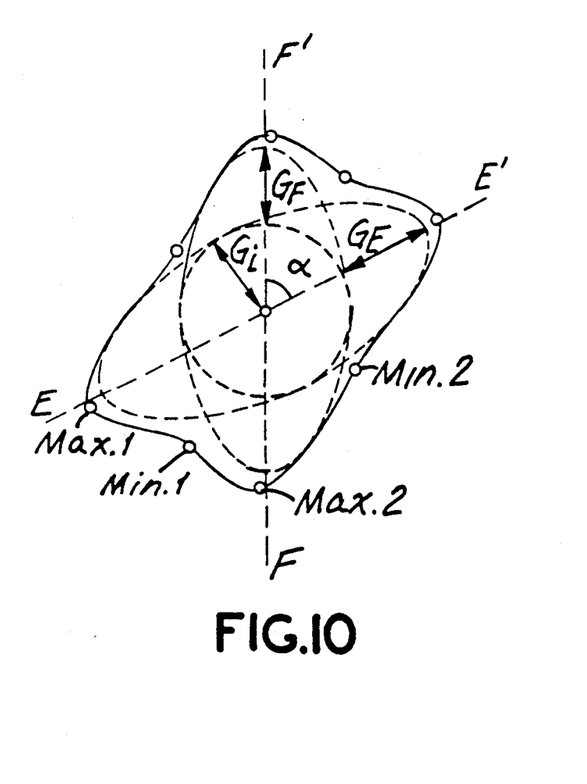
FIG. 10 shows a modulus of elasticity for bidirectional anisotropy.

In the case of bidirectional anisotropy shown in FIG. 10, the modulus of anisotropic elasticity can be determined from a combined elliptional model $$\sigma_{\phi_1} = \sigma \sum_{k=1}^{n} \frac{1}{\sqrt{1 - \Sigma \frac{2}{k} \times \cos^2(\phi - \phi_k)}} - (n-1)$$

and $$\frac{d\sigma_1}{d\phi} = \sigma_1 \sum_{k=1}^{n} \left[ -\frac{1}{2} - \frac{2\Sigma_k^2 \cos\phi - \phi_{11} - \sin\phi - \phi_1}{1 - \Sigma_k^2 \cos^2((\phi - \phi_k)3.2)} \right] = 0$$

where
n = number of ellipses (= 2)
$\phi_k$ = the direction of the longer axis of an ellipse in polar coordinates, and
$\Sigma_k =$ $$\sqrt{\frac{1 - \sigma^2 i}{\sigma_k^2}}$$

the excentricity of an ellipse.

It is obvious from the above equation that the direction of fibers does not necessarily coincide with the direction of the maximum elasticity.

In the real biological tissues (skin) the values of anisotropic modules of elasticity can be several hundred percents greater than the "basic" isotropic elasticity.

In the case of unidirectional anisotropy an isotropic modulus of elasticity can be determined by a minimum value of a sum modulus of elasticity, i.e.

$$\sigma_i = \sigma_{min}$$

Figure 11:
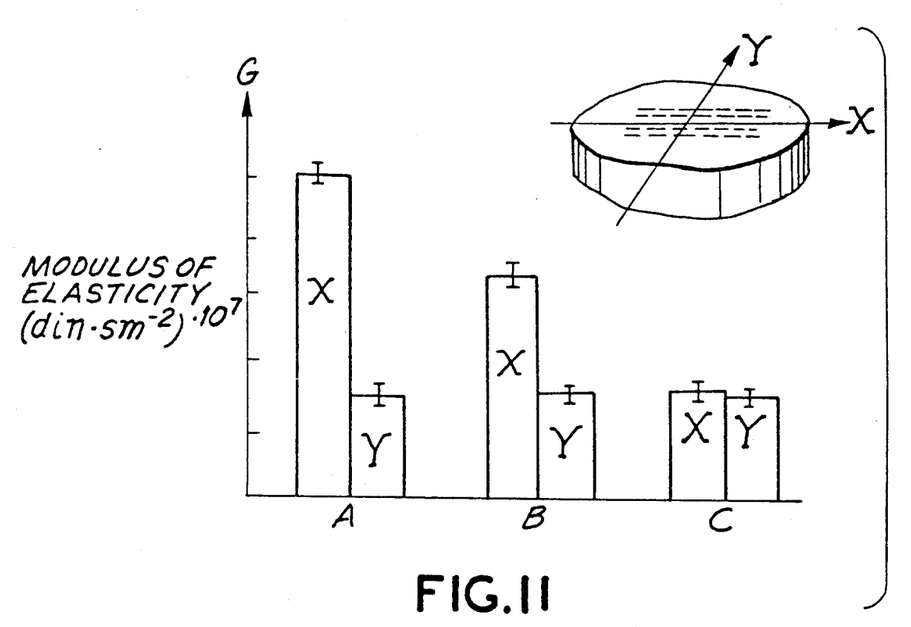
FIG. 11 shows experimental results conducted on gel with implanted fiber structures.

Experimental results can serve as a proof of this fact. An experiment was conducted on gel with implanted fiber structures as shown in FIG. 11. In experimental media A, there are 20 fibers in 1 mm, in experimental media B there are 10 fibers in 1 mm, and in experimental media C, there are no fibers. Letters X and Y represent directions along and transversally to the fiber. Numbers 1 and 2 represent respective measurements in the direction perpendicular to the direction of fibers. It can be seen from the results presented that the speed of pure shear waves within the range of the experiments does not depend on the structure of the fibers and it represents only the elasticity of gel.

The speed of propagation of D-waves depends on the structure of the fibers. If the direction of propagation of D-waves is perpendicular to the direction of the fibers, the speed of D-waves represents also the basic elasticity of gel. If, on the other hand, D-wave propagation direction coincides with the fiber direction, its speed of propagation represents the sum elasticity of gel and fibers.

With the use of D-waves in the direction perpendicular to the direction of the fiber layer one can test the elasticity of the filling and also investigate the contribution of the elasticity of fiber structures and their orientation. From the results it can be seen that a modulus of elasticity determined in a direction perpendicular to the direction of fibers describes the elasticity of a filling media (gel) and it does not depend on the structure of the tissue.

Figure 12:
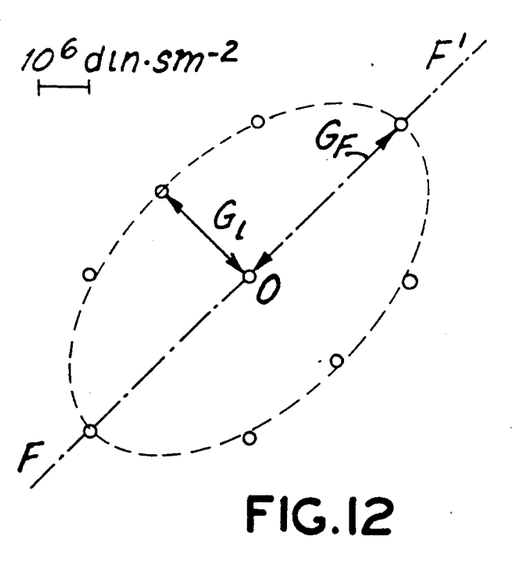
FIG. 12 shows a modulus of elasticity with corresponding speeds of D-waves in human skin in a shoulder area, in polar form.
Figure 13:
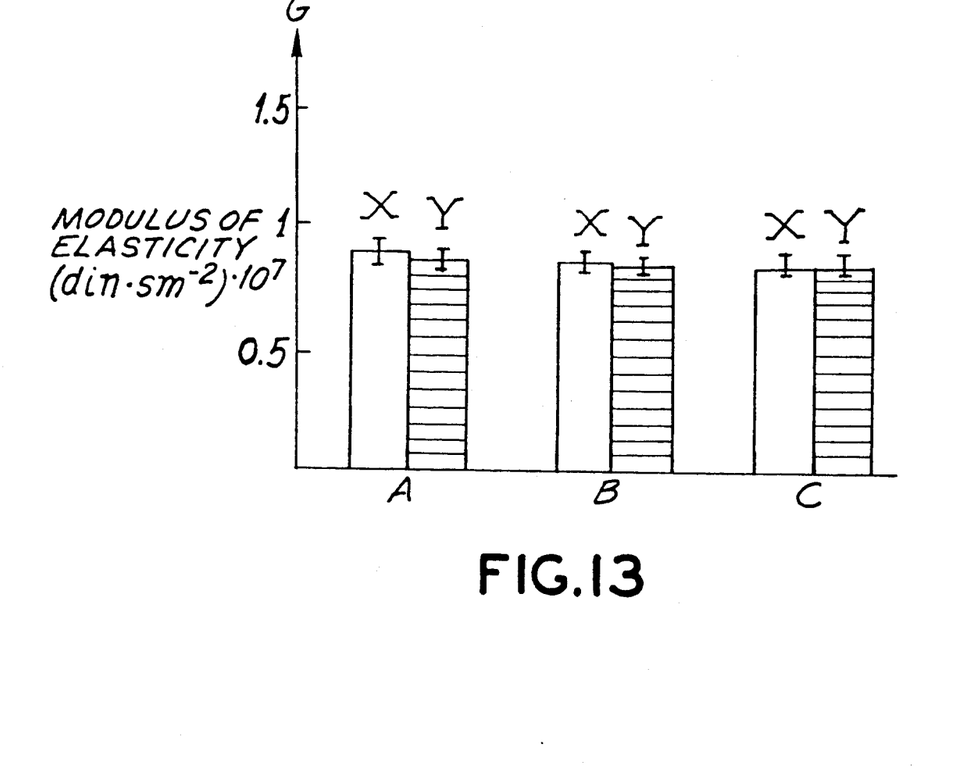
FIG. 13 is a graph showing values of the modulus of elasticity measured by the speed of propagation of pure shear waves.
Figure 14:
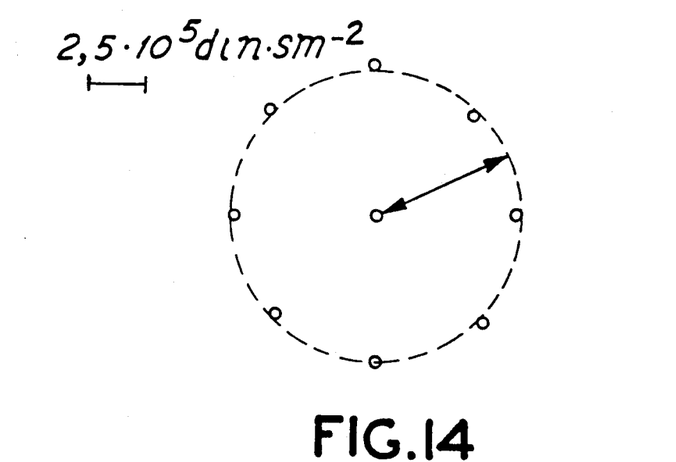
FIG. 14 is another structure of the modulus of elasticity with corresponding speeds of pure shear waves in a human skin in a shoulder area, in polar form.

FIGS. 12 and 14 illustrate the structure of the modulus of elasticity with corresponding speeds of D-waves (FIG. 12) and pure shear waves (FIG. 14) of the human skin in a shoulder area, in polar form.

FIG. 12 shows elliptical characteristics and shows that anisotropic fibrous structures in the skin add to about 70 per cent to the isotropic elasticity of the skin. The direction of fibrous structures coincides with line FF'.

Transmitting occurred in point O and measurements were made at eight directions, 45° apart. The speed of propagation of pure shear waves depends little on the direction of their propagation. The speed of propagation of D-waves depends on the direction of their propagation. It is obvious from the results of measurement of D-waves that we can conclude that the tested skin sample has a fibrous structure, fibers being positioned in the direction F—F' and their contribution to the sum elasticity is about 70 per cent.

One more advantage of the preferred embodiment is that the probe can be applied to a surface of tissue all over the body, without clamping it between the transducers or fixing in any other way.

What is claimed is:

1. A method of noninvasive testing of anisotropic elasticity of a tissue, comprising the steps of:
   inducing on the surface of a tissue being tested a tangential oscillatory deformation;
   measuring, out of all resulting oscillations of particles of the surface of the tissue being tested, only the oscillations which occur in the direction of the induced deformation; and
   determining from a characteristic of said measured oscillations a Young's modulus for said direction and anisotropic characteristics of the elasticity of the tissue being tested.

2. A method of claim 1, wherein said measuring step comprises disposing contact elements of receiving transducers, sensitive to the oscillations of the surface particles of the tissue being tested, along a line which coincides with the direction of the induced deformation and wherein, out of the oscillations of the surface particles of the tissue being tested, only the oscillations which are in the direction of the inducing deformation are measured by means of said receiving transducers.

3. A method of claim 2, wherein the receiving transducers are disposed so that their maximal sensitivity is, for the dislocation of the particles on the surface of the tissue being tested, in the direction of the induced deformation.

4. The method of claim 2, wherein anisotropic characteristics of the tissue being tested are determined by multiple changes of the direction of the induced oscillation deformation, disposition of said receiving transducers and orientation thereof on said surface, and determining, for all possible directions of oscillation deformations on the surface of the tissue, a distribution of the Young's modulus and the direction and elasticity of anisotropic structures.

5. The method of claim 4, wherein the directions of anisotropic structures and corresponding moduli of elasticity are determined by a mechanical model of anisotropic structures, which comprises a combination of discrete elastic elements.

6. A device for noninvasive acoustical testing of anisotropic elasticity of a tissue, comprising one deformation-inducing bimorphous piezotransducer and two receiving bimorphous piezotransducers, all adapted to be disposed vertically to a surface of the tissue being tested and support means for supporting said transducers in such a way that working ends of contact elements of said transducers are parallel to each other.

7. The device of claim 6, wherein the contacting elements of said bimorphous piezotransducers are positioned on one line which coincides with the direction of oscillations thereof.

8. The device of claim 6, wherein the contact elements of the receiving bimorphous piezotransducers are disposed symmetrically with regard to the contact element of the inducing bimorphous piezotransducer.

9. The device of claim 6, wherein the receiving bimorphous piezotransducers are disposed on a common elongated support by means of elastic bearings and the inducing piezotransducer is placed on a second elongated support by means of an elastic bearing.

10. The device of claim 9, wherein the elongated supports of the bimorphous piezotransducers are made in the form of acoustical lines and are fixed on a common mounting support.

11. The device of claim 6, which is equipped with a device for normalization of a pressure of said piezotransducers on the surface of the tissue being tested.

* * * * *